United States Patent [19]
Medoff

[11] Patent Number: 5,931,839
[45] Date of Patent: *Aug. 3, 1999

[54] PIN PLATE FOR FIXATION OF BONE FRACTURES

[76] Inventor: Robert J. Medoff, 159 Ku'ukama St., Kailua, Hi. 96734

[ * ] Notice: This patent issued on a continued prosecution application filed under 37 CFR 1.53(d), and is subject to the twenty year patent term provisions of 35 U.S.C. 154(a)(2).

[21] Appl. No.: 08/590,918

[22] Filed: Jan. 24, 1996

[30] Foreign Application Priority Data

Jan. 27, 1995 [SE] Sweden ................................. 9500285

[51] Int. Cl.⁶ .................................................. A61B 17/80
[52] U.S. Cl. ................................................. 606/69; 606/72
[58] Field of Search ............................... 606/69, 70, 71, 606/72, 73, 61, 60

[56] References Cited

U.S. PATENT DOCUMENTS

| | | | |
|---|---|---|---|
| 3,716,050 | 2/1973 | Johnston | 606/69 |
| 3,779,240 | 12/1973 | Kondo | 606/69 |
| 4,565,193 | 1/1986 | Streli | 606/69 |
| 5,085,660 | 2/1992 | Lin | 606/73 |
| 5,197,966 | 3/1993 | Sommerkamp | 606/69 |
| 5,304,180 | 4/1994 | Slocum | 606/69 |
| 5,484,439 | 1/1996 | Olson et al. | 606/65 |
| 5,534,027 | 7/1996 | Hodorek | 623/16 |
| 5,578,036 | 11/1996 | Stone et al. | 606/69 |
| 5,586,985 | 12/1996 | Putnam et al. | 606/69 |

FOREIGN PATENT DOCUMENTS

| | | |
|---|---|---|
| 2158716 | 3/1991 | United Kingdom . |
| 1300449 | 4/1993 | United Kingdom . |

*Primary Examiner*—Guy V. Tucker
*Attorney, Agent, or Firm*—Ladas & Parry

[57] ABSTRACT

The present invention relates to an implantable element for fixation of one or more fractured bone fragments (9) to a stable bone fragment (10). The element comprises a pin plate (1), which is fixed to the stable bone fragment (10) by one or more screws (7) or the like. To fixate the loose bone fragments (9) one or more pins (8) are passed through holes (3) in the pin plate (1), through the loose bone fragments and further into the stable bone fragment (10). The end of the pin is locked to the pin plate (1) in any suitable way. The form of the pin plate (1) is adapted to the intended site of use.

11 Claims, 2 Drawing Sheets

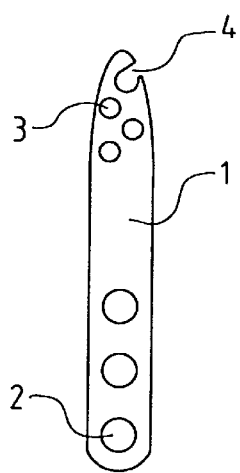
Fig. 1
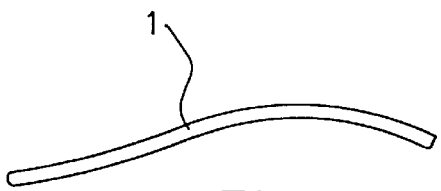
Fig. 2
fig. 3
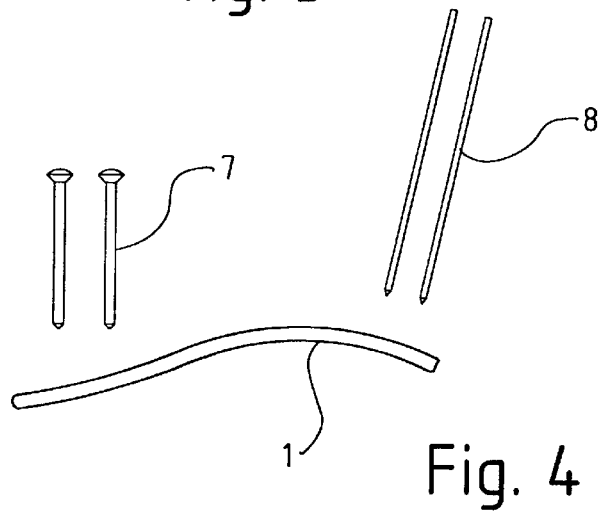
Fig. 4
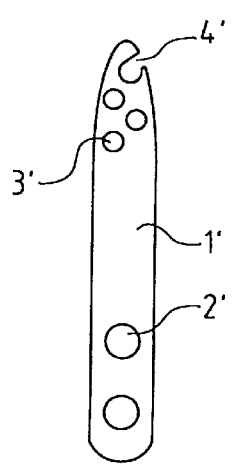
Fig. 7a
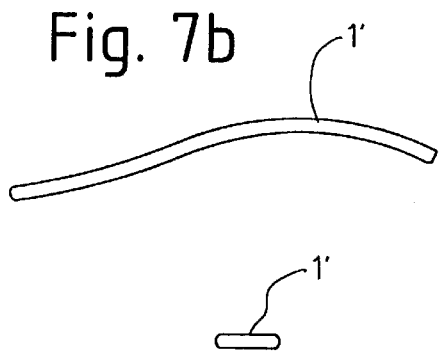
Fig. 7b
Fig. 7c

PIN PLATE FOR FIXATION OF BONE FRACTURES

FIELD OF THE INVENTION

The present invention relates to an implantable means, in the form of a pin plate, for fixation of bone fractures.

BACKGROUND

A fracture near a joint has always been difficult to treat, as the ideal treatment is to achieve rigid fixation of the fracture fragments while allowing nearly immediate motion of the joint.

In order to simplify the description the present invention is described in connection with fractures of the wrist, and particularly those fractures collectively referred to as Colles' fractures. A person skilled in the art will appreciate that the invention is also applicable in fixation of other bones. Possible other bones include, but are not limited to, the distal or lower end of the humerus, the lower tibia and the lower fibula. This requires a change of the shape of the device for each specific area, but the same principles are used irrespective of the site of the fracture. However, the major use of the invention is thought to be for fixation of Colles' fractures.

Treatment of distal radius fractures has been a problem, both because of the frequency of the injury as well as the difficulty in treating them. The goal of treatment is to restore joint congruity and anatomy, minimize the risk of arthritis, and maximize joint mobility. However, although these injuries are almost always treated on an outpatient basis, they typically result in stiffness, arthritis, and diminished function.

There are today essentially four general groups of options available for the treatment of Colles' fractures: (1) closed reduction and casting, (2) external fixation, (3) open reduction and internal fixation, and (4) percutaneous pinning and/or limited open pinning. Each method has its limitations; each has its benefits.

Closed reduction simply involves setting or aligning the broken bone manually and applying a cast to the arm. This treatment avoids any trauma associated with surgery, and is inexpensive. However, it has several disadvantages. It involves cast immobilization until healing of the bone fragments occurs; this frequently results in considerable stiffness. This stiffness is not just confined to the wrist and forearm. Immobilizing the arm in an elderly individual frequently also results in considerable stiffness to the fingers, elbow, and shoulder as well. In addition, this technique is very limited in its ability to hold all but the simplest, most stable fracture patterns in proper alignment. Unstable fractures commonly redisplace during healing, which can lead to arthritis and pain.

External fixation involves the application of relatively large diameter pins inserted into the finger metacarpals and into the radius above the fracture. These pin clusters are then connected with a bar or frame, essentially "bypassing" the fracture site. Typically, two pins are placed in the hand, and two pins in the radius. The frame may distract the wrist as well, in order to assist with fracture reduction, by using the soft tissue sleeve around the fracture to help squeeze the fragments into position. Although external fixation has its proponents, it has its problems. The wrist and hand are rigidly held by the frame, and the pins through the skin tend to irritate the tendons and cause scarring. These problems together cause considerable stiffness in both the wrist and the fingers; frequently the functional loss of grip can be more disabling than the fracture. Pin site infections may also occur and compromise results. External fixation may not achieve an anatomic reduction of the fragments. Currently, external fixation is used for more severely comminuted, fragmented fractures.

Open reduction involves making an incision over the wrist reducing the fragments, and applying plates, screws, and pins as needed. For the Colles' fracture open reduction and internal fixation is seldom used, for several reasons. First, the trauma associated with the dissection and exposure can lead to scarring of the tendons, loss of gliding, and stiffness. Second, the dissection can compromise the blood supply to the fragments, which can result in delayed unions and occasionally non-unions. Third, the fragments tend to be small and osteoporotic; drilling holes and placing screws frequently fragments these pieces further, making anatomic reduction even more difficult. Fourth, most of the fragments and displacement in the typical Colles' fracture are on the dorsal side, and the irregularity of the radius in this area together with the many tendons found near the bone on this side makes it undesirable to place plates and screws dorsally. Finally, these fractures are often comprised of numerous small pieces which must be reduced in a jigsaw puzzle type of arrangement, not easily treated by plate and screw fixation.

Percutaneous pinning involves the placement of small stiff pins, also called K-wires, across fragments of the fracture. The pins may be inserted directly through the skin while imaging the fracture with a fluoroscopy unit. Limited small incisions may also be used. Typically, pin diameters range from 0.035" to 0.062", with the 0.045" and 0.054" pin sizes commonly used in the U.S.A. Pinning has certain advantages. Using a percutaneous or limited open technique to pin fragments allows the fracture to be internally fixed. This provides some additional stability internally which is not available when the fracture is treated with a cast alone. The fragments in these fractures tend to be small and the bone osteoporotic. As a result, pins are more appropriate as a type of fixation than screws in this setting. A small diameter pin has less chance of weakening the fragment and comminuting it further compared with screw holes that are made with even small diameter bone screws.

Pinning, however, has its problems. In order to secure a fragment, there must be a stable bone nearby for securing the pin. Frequently, the only stable piece of bone is the proximal fragment, which may be some distance and at a difficult angle away from the fragment to be pinned. Since the pins have a small diameter, they are likely to bend or displace if the stable piece of bone is relatively far from the fracture fragment. This reduces the ability of the pin to maintain the position of the fragment and, in turn, impedes the process of healing.

In certain cases multiple fragments are put together like stacking cards, by fixing one fragment to a stable proximal piece, and then pinning a second fragment to the first piece, which is assumed to be stabilized by the first pin. This frequently makes the entire assembly dependent upon one or two pins which may engage the stable proximal cortex at some distance from the fracture fragment. Such situations are often unstable.

Another problem with pinning is that the stable piece of bone that the fragment is pinned to has to be located on the opposite cortex from where the pin is inserted. If the only nearby solid piece of bone is located on the cortex adjacent to the fracture fragment, pinning becomes a geometric impossibility. This situation occurs frequently when a dorsal ulnar fragment occurs. If the opposite volar radial surface is fractured in such cases as is often the case, there is no stable cortex available to the angles of pin insertion that are technically feasible.

Examples of these problems with pinning are often encountered in treatment of Colles' fractures involving a radial styloid fragment fixed by a percutaneous trans-styloid pin. The fracture is reduced, and the fluoroscopy unit is used to pass a pin through the radial styloid on an angle to engage the ulnar cortex proximal to the distal fragment. The ability of the pin to hold the radial styloid fracture fragment in an appropriate position is dependent upon the fixation of the pin in the stable proximal ulnar cortex. Since the distance to this fixation site is quite far, and because the small diameter of the pin permits bending, small angular deflections of the pin in its site of purchase at the proximal fragment may lead to significant displacements of the fractured radial styloid.

Because pins have a strong tendency to bend and displace due to motion of the joint, pins are hardly ever used without casting. This means that the patient is still subjected to the common complications of stiffness and loss of function that is associated with the cast.

Ideally the treatment of distal radius fractures should have the same goal as treatment of any other fracture near a joint, namely, achieving rigid fixation of the fracture fragments while allowing nearly immediate mobility of the joint. As can be seen from this discussion, none of the current methods of treatment achieves this goal. Pins alone do not provide adequate stability by themselves and still require a cast. External fixation allows rigid fixation, but does not allow direct reduction of the fracture site, and is associated with considerable morbidity from the complications of stiffness. Closed reduction may cause stiffness as well, and frequently fails to preserve anatomic reduction.

One primary objective of the present invention is to satisfy the goal of providing rigid fixation of fracture fragments while allowing immediate motion of a joint. This objective is satisfied using the technique disclosed in the characterizing clause of the independent claim which follows. The means according to the invention provides an implantable way of constraining by direct contact one or more pins which have been placed to secure fractured bone fragments.

Expedient embodiments of the present invention are disclosed in the dependent claims.

The present invention will now be described in greater detail hereinbelow, with the aid of embodiments shown in the drawings. In the accompanying drawings:

BRIEF DESCRIPTION OF THE DRAWINGS

FIG. 1 is a top view of a radial pin plate according to one embodiment of the invention;

FIG. 2 is a side view of the pin plate of FIG. 1;

FIG. 3 is an end view of the pin plate of the previous Figs.;

FIG. 4 is an exploded view of one embodiment of the invention;

FIGS. 7a–7c are top, side and end views, respectively, of an ulnar pin plate according to the invention.

DETAILED DESCRIPTION OF PREFERRED EMBODIMENTS

Figure 5:
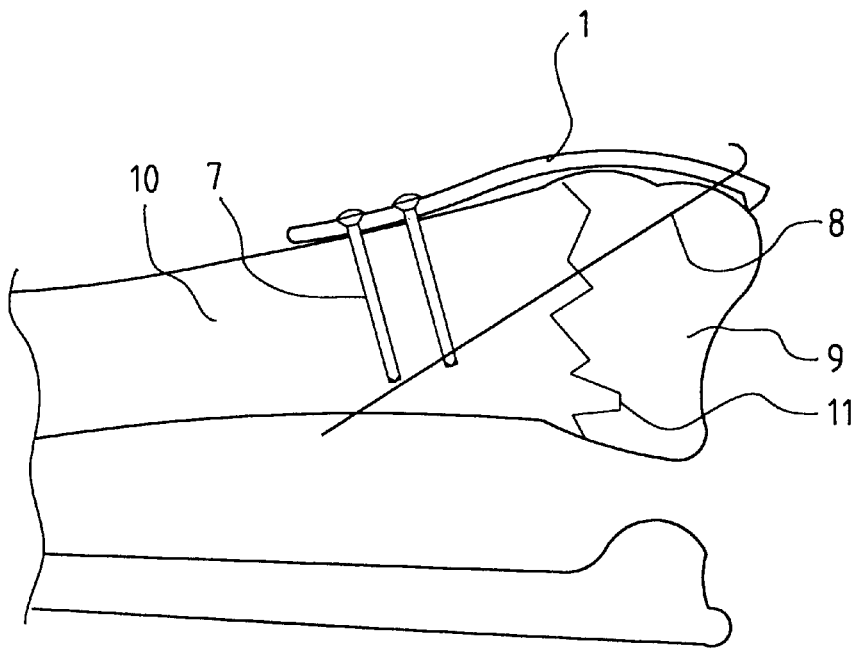
FIG. 5 shows one embodiment of the invention fixed to the radius.

As used herein the expression "pin" also covers wire, nail with head or headless, a thin screw, a threaded pin, pins with bent parts, pins having a head, pin with nut etc., as well as pins with small beads either cut or welded at one side. The beads are placed on the side of the shaft of the pin or at one end of the pin. The difference between "pins" and "wires" in this case is only the diameters, small diameter ones are called wires and larger diameter ones are called pins. Thus, to simplify the description the term "pin" is intended to cover all of the above and similar devices in the description hereinbelow.

Furthermore, the expression "fastening screws" is used for simplicity in the description of securing the plate to bone, but the fastening means are not limited to screws. In other embodiments pins, wires, blades, staples, brackets, or indirect coaption with another device securely attached to the stable bone fragment through holes in the plate are used.

In the embodiment of the invention shown in FIGS. 1 to 5 the implant consists of a pin plate 1 having apertures 2, 3 for fastening screws 7 or pins 8, respectively. One or more of the holes 3 for receiving pins 8 is in some embodiments furnished with slots 4 for insertion of the pins 8 in a way to be described below. In some embodiments the holes 3 are chamfered to facilitate the insertion of the pins 8.

The pin plate 1 is designed to have a form adapted to the intended place of use. The general form of the radial pin plate 1 is apparent from FIGS. 1 to 3. As is apparent from FIGS. 4 and 5 the upper part of the radial pin plate 1 follows the form of the radial styloid and has a straight cross-section in end view. The lower part of the pin plate 1 has a semicircular cross-section in end view (FIG. 3) to match the form of the radius on the dorsal side.

Separate left and right pin plates 1 are furnished as well as pin plates with varying lengths. In the embodiment of the drawings the pins 8 have a circular cross-section. In other embodiments of the invention the pins 8 have other cross-sections, such as triangular, quadrangular, trapezoid etc. Furthermore, in some embodiments the lower part of the pins far end have one cross-section, e.g. round, and the upper part another cross-section, e.g. quadrangular. In order to match pins 8 with different diameters various plate hole sizes are available. In one embodiment the pin plate 1 is furnished with holes 3 accepting pins 8 with different diameters. The actual dimensions to be used is decided by the surgeon in each case based on the specific circumstances such as fracture site, fragment size, bone condition etc.

FIGS. 7a to 7c show one embodiment for an ulnar pin plate 1', i.e. a pin plate 1' adapted for use on the ulna. The most apparent difference between the radial pin plate 1 and the ulnar pin plate 1' is the form of the cross-section in end view. The lower part of the ulnar pin plate 1' has a straight cross-section (FIG. 7c). Apart from the somewhat different form the ulnar pin plate 1' displays the same features as the radial pin plate 1. Thus, the ulnar pin plate 1' has apertures 2', 3' and a slot 4' for cooperation with fastening screws and pins, respectively.

The rigidity of pin fixation of the fracture fragment is considerably improved by having it pass through one of the small holes 3 and possibly a tight slot 4 in the pin plate 1 which has been secured to the proximal fragment 10. After the pin 8 is placed, it can be bent over the superficial surface of the plate 1 to keep it from migrating. The pin 8 now has two point fixation, and fragment stability is greatly enhanced. In addition, the plate can serve an additional role as a buttress to the distal fragment 9.

The pin plate 1 is securely fixed proximally with one or more screw(s) 7, pin(s), wire(s), blade(s), staple(s) bracket (s) or indirect coaptation with another device to the stable bone fragment through holes in the plate. The plate has distally holes 3 through which the pin 8 is passed; additionally, these holes 3 may or may not have slots 4.

If a hole 3 with a slot 4 at the distal portion 5 of the plate 1 is used, the pin 8 will be placed first, and the plate 1 slid along the surface of the bone 10 to engage the pin 8. In one embodiment the entrance slot 4 is slightly undersized, and capable of slight widening as the pin passes through the slot. This way, the plate 1 will "snap" as the pin 8 is passed into the slot 4, preventing disengagement. Once the plate 1 is snapped over the pin 8, the pin 8 is bent to further secure it, and the plate 1 is fixed proximally with one or two screws 7 or other means of fixation, as indicated above.

Normally the pin, or K-wire, is placed on a high speed drill type apparatus, known as a pin driver, or it may be placed on a standard sterile operating room drill. In different embodiments the tip of the pin is either a trochar type, or narrows to a flattened region near the end which ends in a point. Some designs have a cutting type drill bit on the end. Thus, the tip of the pin acts like a drill and allows the tip to cut through bone as it is inserted.

The fixation of the pins 8 at the pin plate 1 is accomplished in different ways in different embodiments of the invention. In one embodiment the pins 8 are bent over the superficial surface of the plate 1 as stated above. In another embodiment threaded pins 8 are used which pass through threaded holes within the plate 1. Optionally, the pins 8 are locked with locking means such as a locking nut. This provides fixation of the pin 8 in space in both a transverse plane (in the plane of the plate 1) and an axial plane (along the axis of the pin 8). This variation further allows a pin 8 to be placed which only purchases the single adjacent cortex, fixing it in space relative to the position of the plate 1.

In a further embodiment (not shown) the openings 3 for receiving the pins 8 are slightly undersized with a cut extending from the hole 3 to the edge of the plate 1. In this design the pin 8 is captured at the site of insertion due to the compression of the surrounding undersized hole. In this situation, a three-pointed clamp is applied to the plate to place a bending torque on the plate centered at the site of the pin hole 3; this allows the hole 3 to be enlarged or opened up slightly, enough so that it allows placement of the pin 8 through the hole 3. When the clamp is released, the hole 3 returns to its normal outer diameter, holding the pin 8.

Alternatively, a slotted hole 3 is used which joins a slightly undersized hole 3, instead of a slightly larger hole. In this circumstance, as the pin 8 is snapped into the hole 3, it is effectively locked into place.

In a further embodiment (not shown) the pin plate 1 is furnished with one or more threaded studs. The pin 8 is hooked around one stud and locked against the pin plate 1 with a threaded locking nut on the stud. Instead of locking the pin around the stud, the stud may have a slot for receiving the pin 8. After the pin has been placed in the slot a locking nut is screwed onto the stud to lock the pin 8 in the slot of the stud.

The focus of this device is in securing a trans-styloid radial pin 8. It makes the fixation of this fragment secure enough so that a cast is not necessary in most cases. Each plate 1 allows one or more pins 8 in the distal end. The number of pins 8 used and their angle of insertion is decided in each case by the surgeon depending on the site and size of the specific fracture or fractures. In some instances the pin 8 is inserted through the fragment to engage a stable piece of bone on the other side of the fragment. In other instances the pin is only inserted in the adjacent cortex.

In FIG. 5 a pin plate 1 according to the invention is shown in an embodiment for fixation of a trans-styloid pin 8.

Figure 6:
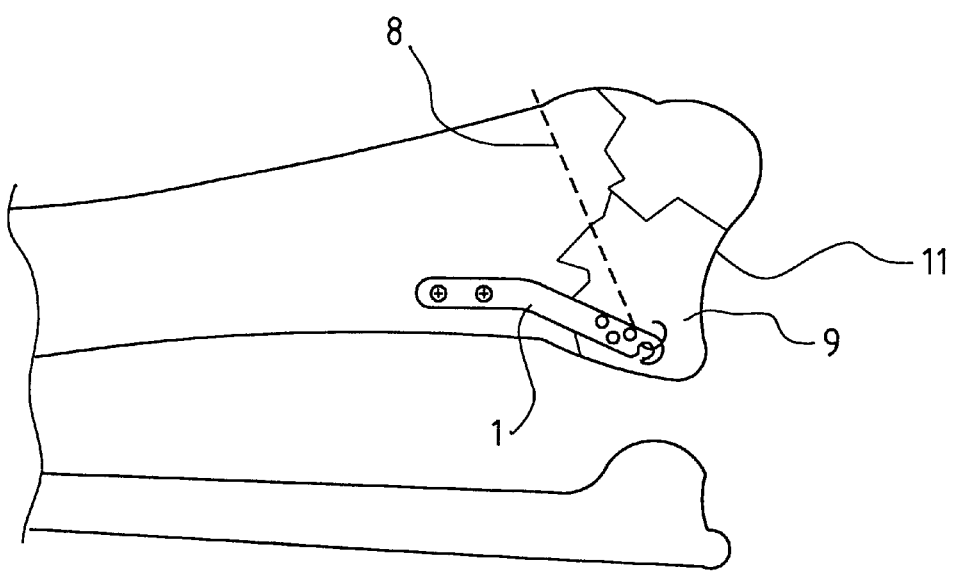
FIG. 6 shows one embodiment of the invention fixed in an alternative location to the radius.

In FIG. 6 an alternative pin plate 1 is shown with a design to match the contour of the bone at the ulnar, dorsal side of the distal radius. This pin plate 1 is intended for use when there is a need to place a pin from that side of the distal radius.

The implant of the invention has further applicability in fixation of other bones besides the radius.

The above detailed description has referred to but a limited number of embodiments of the present invention, but it will be readily perceived by a person skilled in the art that the present invention encompasses a large number of embodiments without departing from the spirit and scope of the appended claims.

I claim:

1. An implantable device for fixation of at least one fractured bone fragment to a stable bone fragment, said implantable device comprising an implantable plate having opposite end portions, fastening means for securing one end portion of said plate to stable bone, at least one fixation pin for penetrating said at least one fractured bone fragment, and traversing a fracture for entering the stable bone fragment and for being secured therein at a stable fixation site at a far end of said fixation pin, the opposite, near end of said pin being adapted for extending from the fractured bone fragment, said near end of said pin being engageable in one of a plurality of holes in the other end portion of the plate, said holes in said plate providing means for allowing the pin to slide axially therein but preventing compression across the fracture, and stabilizing said near end of the pin against displacement in the plane of the plate.

2. The device of claim 1, wherein at least one of said holes is located in said plate for being adjacent to an entrance of penetration of said at least one pin into said bone fragment.

3. The device of claim 1, comprising a slot in said plate extending from said one of said holes to an edge thereof to enable insertion of said at least one pin into said hole via said slot.

4. The device of claim 3, wherein said slot is slightly undersized with respect to said pin to provide snap engagement of said pin in said hole.

5. The device of claim 1, wherein said plate includes means for providing a snap engagement of said at least one pin in said hole.

6. The device of claim 5, wherein said means which provides snap engagement is constructed to permit said plate to be engaged on said at least one pin after the pin has been introduced into a fractured bone fragment.

7. The device of claim 1, wherein said end portions of said plate are shaped to conform to the respective shapes of said stable and fractured bone fragments.

8. The device of claim 1, wherein said fastening means for securing the plate to the stable bone fragment comprises a rigid fastener in the form of at least one screw, pin, wire, blade, staple, bracket, or indirect coaptation device adapted to be secured to the stable bone fragment with compression.

9. The device of claim 1, wherein said near end of said at least one pin is bendable back to face said plate and prevent separation of the plate and the pin.

10. The device of claim 1, wherein said pin has a smooth bone-engaging portion for penetrating into the fractured bone fragment.

11. The device of claim 1, wherein said at least one pin has a diameter between 0.035" and 0.062" and is bendable by hand.

* * * * *

US005931839C1

(12) EX PARTE REEXAMINATION CERTIFICATE (8498th)
United States Patent
Medoff

(10) Number: US 5,931,839 C1
(45) Certificate Issued: Aug. 30, 2011

(54) PIN PLATE FOR FIXATION OF BONE FRACTURES

(75) Inventor: Robert J. Medoff, Kailua, HI (US)

(73) Assignee: Trimed, Inc., Valencia, CA (US)

Reexamination Request:
No. 90/011,119, Jul. 29, 2010

Reexamination Certificate for:
Patent No.: 5,931,839
Issued: Aug. 3, 1999
Appl. No.: 08/590,918
Filed: Jan. 24, 1996

(30) Foreign Application Priority Data

Jan. 27, 1995 (SE) ............................................. 9500285

(51) Int. Cl.
*A61B 17/80* (2006.01)
*A61B 17/68* (2006.01)

(52) U.S. Cl. ..................... 606/286; 606/329; 606/902
(58) Field of Classification Search ................ 606/69
See application file for complete search history.

(56) References Cited

U.S. PATENT DOCUMENTS

| 2,414,882 | A | 1/1947 | Longfellow |
| 2,526,959 | A | 10/1950 | Lorenzo |
| 5,190,544 | A | 3/1993 | Chapman et al. |
| 5,484,439 | A | 1/1996 | Olson et al. |

FOREIGN PATENT DOCUMENTS

GB 2245498 1/1992

OTHER PUBLICATIONS

Gary Clancey, "Percutaneous Kirschner–Wire Fixation of Colles Fracture," The Journal of Bone and Joint Surgery, Sep. 1984, pp. 1008–1014, vol. 66–A, No. 7.
Waldemar Link's "May Anatomical Bone Plates" Product Brochure.
Stephen Leibovic et al., "Treatment of Complex Intra–Articular Distal Radius Fractures," Orthopedic Traumatology: Complex Fractures and Associated Injures, Oct. 1994, pp. 685–706, vol. 25, No. 4.
Waldemar Link Advertisement for May Anatomical Bone Plates appearing in The Journal of Bone And Joint Surgery, Dec. 1990, vol. 79–A, No. 10.

*Primary Examiner*—David O. Reip

(57) ABSTRACT

The present invention relates to an implantable element for fixation of one or more fractured bone fragments (9) to a stable bone fragment (10). The element comprises a pin plate (1), which is fixed to the stable bone fragment (10) by one or more screws (7) or the like. To fixate the loose bone fragments (9) one or more pins (8) are passed through holes (3) in the pin plate (1), through the loose bone fragments and further into the stable bone fragment (10). The end of the pin is locked to the pin plate (1) in any suitable way. The form of the pin plate (1) is adapted to the intended site of use.

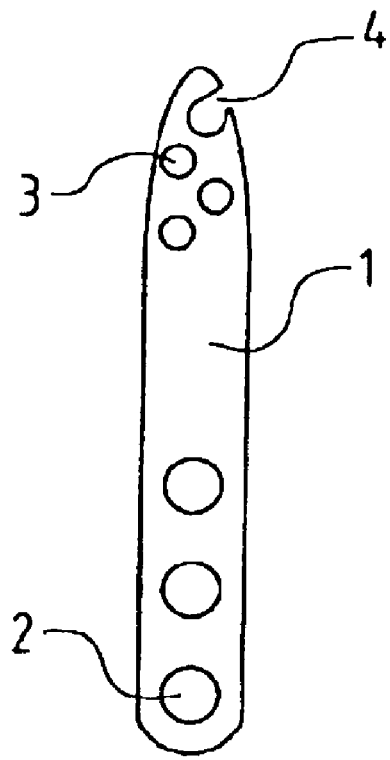

US 5,931,839 C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 4, lines 23-30:

The pin plate 1 is designed to have a form adapted to the intended place of use. The general form of the radial pin plate 1 is apparent from FIGS. 1 to 3. As is apparent from FIGS. 4 and 5 the upper part of the radial pin plate 1 follows the forms of the radial styloid and has a straight cross-section in end view. The lower part of the pin plate 1 has a semicircular cross-section in end view (FIG. 3) to match the form of tha radius on the dorsal side. *The pin plate 1 is directed through an incision at the fracture site.*

Column 5, lines 58-67:

The focus of this device is in securing a trans-styloid radial pin 8. It makes the fixation of this fragment secure enough so that a cast is not necessary in most cases *and the fracture can be treated and healed, with the incision closed at the fracture site without maintaining compression across the fracture*. Each plate 1 allows one or more pins 8 in the distal end. The number of pins 8 used and their angle of insertion is decided in each case by the surgeon depending on the site and size of the specific fracture or fractures. In some instances the pin 8 is inserted through the fragment to engage a stable piece of bone on the other side of the fragment *and is the only component that traverses the fracture*. In other instances the pin is only inserted in the adjacent cortex.

AS A RESULT OF REEXAMINATION, IT HAS BEEN DETERMINED THAT:

Claim 1 is cancelled.

Claims 2 and 7-11 are determined to be patentable as amended.

New claims 12-37 are added and determined to be patentable.

Claims 3-6 were not reexamined.

2. The device of claim [1] *13*, wherein at least one of said holes is located in said plate for being adjacent to an entrance of penetration of said at least one pin into said bone fragment.

7. The device of claim [1] *13*, wherein said end portions of said plate shaped to conform to the respective shapes of said stable and fractured bone fragments.

8. The device of claim [1] *13*, wherein said fastening means for securing the plate to the stable bone fragment comprises a rigid fastener in the form of at least one screw, pin, wire, blade, staple, bracket, or indirect coaptation device adapted to be secured to the stable bone fragment with compression.

9. The device of claim [1] *13*, wherein said near end of said at least one pin is bendable back to face said plate and prevent separation of the plate and the pin.

10. The device of claim [1] *13*, wherein said pin has a smooth bone-engaging portion for penetrating into the fractured bone fragment.

11. The device of claim [1] *13*, wherein said at least one pin has a diameter between 0.035" and 0.062" and is bendable by hand.

*12. An implantable device for fixation of at least one fractured bone fragment to a stable bone fragment, said implantable device comprising an implantable plate having opposite end portions, fastening means for securing one end portion of said plate to stable bone, at least one fixation pin for penetrating said at least one fractured bone fragment, and traversing a fracture for entering the stable bone fragment and for being secured therein at a stable fixation site at a far end of said fixation pin, the opposite, near end of said pin being adapted for extending from the fractured bone fragment, said near end of said pin being engageable in one of a plurality of holes in the other end portion of the plate, said holes in said plate providing means for allowing the pin the slide axially therein but preventing compression across the fracture, and stablilizing said near end of the pin against displacement in the plane of the plate, wherein the plate and near end of the pin cooperate to provide fixation of the pin at the plate along an axis of the pin.*

*13. An implantable device for fixation of at least one fractured bone fragment to a stable bone fragment, said implantable device comprising an implantable plate having opposite end portions, fastening means for securing one end portion of said plate to stable bone, at least one fixation pin for penetrating said at least one fractured bone fragment, and traversing a fracture for entering the stable bone fragment and for being secured therein at a stable fixation site at a far end of said fixation pin, the opposite, near end of said pin being adapted for extending from the fractured bone fragment, said near end of said pin being engageable in one of a plurality of holes in the other end portion of the plate, said holes in said plate providing means for allowing the pin the slide axially therein but preventing compression across the fracture, and stablilizing said near end of the pin against displacement in the plane of the plate, wherein the plate and near end of the pin cooperate to provide fixation of the pin at the plate in space in the plane of the plate.*

*14. The device of claim 13, wherein the pin is a K-wire.*

*15. An implantable device for fixation of at least one fractured bone fragment to a stable bone fragment, said implantable device comprising an implantable plate having opposite end portions, fastening means for securing one end portion of said plate to stable bone, at least one fixation pin for penetrating said at least one fractured bone fragment, and traversing a fracture for entering the stable bone frag-* ment and for being secured therein at a stable fixation site at a far end of said fixation pin, the opposite, near end of said pin being adapted for extending from the fractured bone fragment, said near end of said pin being engageable in one of a plurality of holes in the other end portion of the plate, said holes in said plate providing means for allowing the pin to slide axially therein but preventing compression across the fracture, and stabilizing said near end of the pin against displacement in the plane of the plate, wherein the plate and near end of the pin fixedly cooperate to prevent migration of the near end of the pin in the plane of the plate.

16. An implantable device for allowing treatment of a bone fracture by fixation of at least one fractured bone fragment to a stable bone fragment, said implantable device comprising an implantable plate having opposite end portions, fastening means for securing one end portion of said plate to stable bone, at least one fixation pin for penetrating said at least one fractured bone fragment, and traversing a fracture for entering the stable bone fragment and for being secured therein at a stable fixation site at a far end of said fixation pin, the opposite, near end of said pin being adapted for extending from the fractured bone fragment, said near end of said pin being engageable in one of a plurality of holes in the other end portion of the plate, said holes in said plate providing means for allowing the pin to slide axially therein but preventing compression across the fracture, and stabilizing said near end of the pin against displacement in the plane of the plate so that the fracture can be treated and healed without maintaining compression across the fracture, wherein the near end of the pin and plate cooperate so that there is a fixation point for the near end of the pin at the plate.

17. The device of claim 16, wherein at least one of said holes is located in said plate for being adjacent to an entrance of penetration of said at least one pin into said bone fragment.

18. The device of claim 16, comprising a slot in said plate extending from said one of said holes to an edge thereof to enable insertion of said at least one pin into said hole via said slot.

19. The device of claim 18, wherein said slot is slightly undersized with respect to said pin to provide snap engagement of said pin in said hole.

20. The device of claim 16, wherein said plate includes means for providing a snap engagement of said at least one pin in said hole.

21. The device of claim 20, wherein said means which provides snap engagement is constructed to permit said plate to be engaged on said at least one pin after the pin has been introduced into a fractured bone fragment.

22. The device of claim 16, wherein said end portions of said plate are shaped to conform to the respective shapes of said stable and fractured bone fragments.

23. The device of claim 16, wherein said fastening means for securing the plate to the stable bone fragment comprises a rigid fastener in the form of at least one screw, pin, wire, blade, staple, bracket, or indirect coaptation device adapted to be secured to the stable bone fragment with compression.

24. The device of claim 16, wherein said near end of said at least one pin is bendable back to face said plate and prevent separation of the plate and the pin.

25. The device of claim 16, wherein said pin has a smooth bone-engaging portion for penetrating into the fractured bone fragment.

26. The device of claim 16, wherein said at least one pin has a diameter between 0.035" and 0.062" and is bendable by hand.

27. The device of claim 16, wherein the pin is a K-wire.

28. A method of using an implantable device, the method comprising the steps of:
providing an implantation device for fixation of at least one fractured bone fragment to a stable bone fragment, said implantable device comprising an implantable plate having opposite end portions, fastening means for securing one end portion of said plate to stable bone, at least one fixation pin for penetrating said at least one fractured bone fragment, and traversing a fracture for entering the stable bone fragment and for being secured therein at a stable fixation site at a far end of said fixation pin, the opposite, near end of said pin being adapted for extending from the fractured bone fragment, said near end of said pin being engageable in one of a plurality of holes in the other end portion of the plate, said holes in said plate providing means for allowing the pin to slide axially therein but preventing compression across the fracture, and stabilizing said near end of the pin against displacement in the plane of the plate;
making an incision through a site at which implantation of the device is to be effected;
securing the one end portion of the plate to the stable bone;
directing the pin so that the pin: a) penetrates the at least one fractured bone fragment; b) traverses the fracture; and c) enters the stable bone fragment so as to be secured at the stable fixation site at the far end of the pin;
engaging the near end of the pin in one of the plurality of holes in the other end portion of the plate so that the one of the holes stabilizes the near end of the pin against displacement in the plane of the plate; and
closing the incision without developing compression across the fracture.

29. The method according to claim 28 wherein the one end portion of the plate is secured to the stable bone after directing the pin.

30. The method according to claim 28 wherein the step of directing the pin comprises directing the pin so that the pin extends fully through the at least one bone fragment.

31. The method according to claim 28 wherein the one fractured bone fragment directly engages the stable bone fragment and the step of directing the pin comprises directing the pin so that the pin extends fully through the one bone fragment.

32. The method according to claim 28 wherein the only component that traverses the fracture is the at least one pin after closing the incision.

33. The method for treating a fracture by fixation of at least one fractured bone fragment to a stable bone fragment at a site of the fracture, the method comprising the steps of:

providing an implantable device for fixation of at least one fractured bone fragment to a stable bone fragment, said implantable device comprising an implantable plate having opposite end portions, fastening means for securing one end portion of said plate to stable bone, at least one fixation pin for penetrating said at least one fractured bone fragment, and traversing a fracture for entering the stable bone fragment and for being secured therein at a stable fixation site at a far end of said fixation pin, the opposite, near end of said pin being adapted for extending from the fractured bone fragment, said near end of said pin being engageable in one of a plurality of holes in the other end portion of the plate, said holes in said plate providing means for allowing the pin to slide axially therein but preventing compression across the fracture, and stabilizing said near end of the pin against displacement in the plane of the plate;

making an incision at the fracture site;

securing one of two opposite ends of the plate to the stable bone through a fastening means;

directing the a least one fixation pin so as to: a) penetrate the at least one fractured bone fragment; b) traverse the fracture; and c) enter the stable bone fragment so that the far end of the pin is secured at the stable fixation site on the stable bone fragment;

engaging the near end of the pin extending from the fractured bone fragment in one of the plurality of holes in the other end of the plate so as to stabilize the near end of the pin against displacement in the plane of the plate, the holes providing means for allowing the pin to slide axially therein but preventing compression across the fracture; and closing the incision without developing compression across the fracture.

34. The method according to claim 33 wherein the one end portion of the plate is secured to the stable bone after directing the pin.

35. The method according to claim 33 wherein the step of directing the pin comprises directing the pin so that the pin extends fully through the at least one bone fragment.

36. The method according to claim 33 wherein the one fractured bone fragment directly engages the stable bone fragment and the step of directing the pin comprises directing the pin so that the pin extends fully through the one bone fragment.

37. The method according to claim 33 wherein the only component that traverses the fracture is the at least one pin after closing the incision.

\* \* \* \* \*